United States Patent [19]
Botchan et al.

[11] Patent Number: 5,925,516
[45] Date of Patent: Jul. 20, 1999

[54] MEDICAMENTS FOR THE TREATMENT OF PAPILLOMAVIRUS DISEASES

[75] Inventors: Michael R. Botchan, Kensington; Robin Clark, Oakland; Ian J. Mohr, Berkeley; Shaw Sun, Fremont, all of Calif.

[73] Assignees: Chiron Corporation, Emeryville; University of California, Oakland, both of Calif.

[21] Appl. No.: 08/430,521

[22] Filed: Apr. 27, 1995

Related U.S. Application Data

[62] Division of application No. 07/632,027, Dec. 21, 1990, Pat. No. 5,464,936.

[51] Int. Cl.$^6$ .............................. C12Q 1/68; C07H 17/00; C07K 14/00
[52] U.S. Cl. .................. 435/6; 536/23.72; 536/24.1; 530/300; 530/350
[58] Field of Search .................... 435/7.1, 6; 530/350, 530/300; 536/23.72, 24.1

[56] References Cited

U.S. PATENT DOCUMENTS 5,620,849   4/1997   Botchan et al. ............................. 435/6

FOREIGN PATENT DOCUMENTS

| | | |
|---|---|---|
| 0257754 | 3/1988 | European Pat. Off. . |
| 0258017 | 3/1988 | European Pat. Off. . |
| 0302758 | 3/1989 | European Pat. Off. . |

OTHER PUBLICATIONS

Schiller et al. 1989 J Virol. 63(4): 1775–1782.
Lambert et al. 1988 J Virol 62 (11): 4009–4015.
Blitz et al. "The 68–Kilodalton E1 Protein of Bovine Papillomavirus Is a DNA Binding Phosphoprotein Which Associates with the E2 Transcriptional Activator in Vitro" (1991) *J. Virol.* 65(2):649–656.
Chiang et al. "An E1M+E2C Fusion Protein Encoded by Human Papillomavirus Type 11 Is a Sequence–Specific Transcription Repressor"(1991) *J. Virol.* 65(6):3317–3329.
Knight et al. "The activation domain of the bovine papillomavirus E2 protein mediates association of DNA–bound dimers to form DNA loops" (1991) *Proc. Natl. Acad. Sci. USA* 88:3204–3208 (copy enclosed).
Lambert et al. "Bovine Papillomavirus Type 1 E1 Replication–Defective Mutants are Altered in Their Transcriptional Regulation" (1988) *J. Virol.* 62:4009–4015.
Mohr et al. "Targeting the E1 Replication Protein to the Papillomavirus Origin of Replication by Complex Formation with the E2 Transactivator" (1990) *Science* 250:1694–1699.
Schiller et al. "Identification of Bovine Papillomavirus E1 Mutants with Increased Transforming and Transcriptional Activity"(1989) *J. Virol.* 63:1775–1782.
Sekine et al. "Expression of human papillomavirus type 6b E2 gene product with DNA–binding activity in insect (*Bombyx mori*) cells using a baculovirus expression vector" (1988) *Gene* 65:187–193.
Sun et al. "Identification of a 68–Kilodalton Nuclear ATP–Binding Phosphoprotein Encorded by Bovine Papillomavirus Type 1" (1990) *J. Virol.* 64:5093–5105 (copy enclosed).
Yang et al. "Replication of Bovine Papillomavirus Type 1 DNA Initiates within an E2–Responsive Enhancer Element" (1990) *J. Virol.* 64:5903–5911 (copy enclosed).

*Primary Examiner*—Karen C. Carlson
*Attorney, Agent, or Firm*—Thomas P. McCracken; Robert P. Blackburn

[57] ABSTRACT

Medicaments, and methods of identifying the same, are described that are useful for treating papillomavirus diseases that have the characteristics of preventing, interfering with, or reversing the binding of the appropriate papillomavirus proteins E1 or E2 to a nucleotide sequence homologous to a nucleotide sequence present in the papillomavirus genome, or of the formation of a complex consisting of papillomavirus proteins E1 and E2, or the binding of the complex to the nucleotide sequence.

3 Claims, 5 Drawing Sheets

MEDICAMENTS FOR THE TREATMENT OF PAPILLOMAVIRUS DISEASES

This application is a division of application Ser. No. 07/632,027 filed on Dec. 21, 1990 now U.S. Pat. No. 5,464,936.

FIELD OF THE INVENTION

This invention is in the field of molecular biology with emphasis on the identification of medicaments that can be used to treat papillomavirus diseases, particularly warts and cancers.

BACKGROUND OF THE INVENTION

It has been known for some time that papillomaviruses are responsible for inducing diseases in many higher vertebrates, including humans. Papillomaviruses are small DNA viruses, nonenveloped, that replicate in the nucleus of squamous epithelial cells. They are spread widely throughout nature and are causative of epithelial proliferative lesions particularly, benign fibropapillomas, or as they are more commonly known warts. Papillomaviruses are also implicated in a number of cancers. To date there have been identified about 58 distinct human papillomaviruses, based on the extent and degree of relatedness of their genomes.

The clinical importance of warts varies considerably and determinative factors are the infecting viral type, the location of the wart, and factors unique to the host. For example, a wart located on the skin is often clinically insignificant, being self limiting. However, warts on the vocal cords may be life threatening as a result of respiratory obstruction. The vast majority of skin warts spontaneously regress within a few years after their initial appearance, but may persist for longer times. The exception is a rare life threatening papillomavirus disease termed epidermodyspasia verruciformis. In this disease, the infected individual does not experience spontaneous regression, but rather the infection may progress to a malignant stage. Orth, G. epitermodyspasia verruciformis, in: Salzman, N. P. Howley, P. M. Eds. the papovaviridae, vol. 2, N.Y.: Plenum Press 1987:199–243. The disease is present world-wide, but is rare and is often found among family members. Thus, genetic factors are thought to be involved in the etiology of the disease.

Papillomaviruses are also involved in producing sexually transmitted warts of the genital tract. There is reported to be well over a million cases in the United States alone. Beckter, T. M, Stone, K. M, Alexander, E. R., Genital Human Papillomavirus Infection: A Growing Concern Obstet Gynecol Clin North am 1987: 14:389–396.

As mentioned above, papillomavirus is thought to be responsible for several different types of cancer, including cervical cancer, of which there are about 500,000 new cases diagnosed yearly. Pto, R., Introduction: Geographic Patterns and Trends. in: Peto R., zur Hausen H. Eds. Virol Etiology of Cervical Cancer. BanBury Report 21. Cold Spring Harbor, N.Y.: Cold Spring Harbor Laboratory, 1986;3–15. In addition to cervical cancer, papillomavirus has been implicated as a causative agent in nasal tumors, and various oral cancers.

Warts generally regress spontaneously, and thus patients that seek treatment do so for the relief of temporary pain or discomfort or for cosmetic reasons. Treatments for warts generally consist of the application of cryotherapy, or the use of one or more DNA synthesis inhibitors, or simply removing the warts surgically. Further treatments have consisted of the application of various interferons particularly against refractory genital warts. This approach has been partially successful with cure rates in the range of about 36% compared to spontaneous remissions of 3%.

Part of the explanation for the lack of unified treatment strategies for controlling or curing patients of papillomavirus infections is the inability to grow the virus in vitro, and thus develop a convenient and reliable assay to identify efficacious drugs. For the most part, the study of papillomavirus has come from the development of in vitro transformation assays that has facilitated the identification of viral functions involved in the induction of cellular proliferation. The prototype papillomavirus used in these studies has been bovine papillomavirus type I (BPV-1).

Papillomaviruses consist of double-stranded DNA of about 8,000 base pairs. Sequencing studies based on six animal and nine human papillomaviruses have revealed that the genomic organization of papillomaviruses is remarkably conserved. A key shared feature is that all of the viruses have open reading frames located on one strand of the viral DNA. There are approximately ten open reading frames that have been classified based on their position in the viral genome.

Using BPV-I, genetic studies have shown that papillomavirus plasmid replication relies upon the expression of particular viral early genes. The first such gene to be identified was the E2 trans-activator. Those molecules encoded by the E2 ORF stimulates transcription viral genes possibly through their interaction with enhancers in the so called long controlled region (LCR), a region in which there are no significant open reading frames, and which varies in size depending on the nature of the papillomavirus.

Many other papillomavirus transcriptional regulatory factors have been identified in addition to E2. E6 and E7 are involved in cellular transformation as is E5, which is the smallest of the known transforming proteins. In addition to the role that these early proteins play in viral transformation or transcription, there is data which suggest that they play indirect functions in viral plasmid replication. Indeed, of the early ORFs, only E3 and E4 have not been shown to be involved in viral plasmid replication. The E1 ORF encodes factors that are thought to be directly involved in plasmid replication and it is the largest ORF in the papillornavirus genome, and it is relatively highly conserved among those papillomaviruses whose genomes have been sequenced. At least two proteins are encoded by the E1 ORF. The 5' end of the E1 ORF encodes a protein with an apparent molecular weight of about 23,000 daltons while the protein encoded by 3' end encodes a 68,000 dalton protein. The latter protein is believed to play an essential role in viral DNA replication.

SUMMARY OF THE INVENTION

An object of the instant invention is to describe a method that is useful for identifying medicaments that interfere with papillomavirus replication.

A second object of the invention is the description of an assay employing two early phase papillomavirus proteins, 68 kD E1 and 48 kD E2, that form a E1/E2 complex that is involved in the initiation of viral DNA replication, that allows the identification of medicaments for the treatment of papillomavirus diseases by their capacity to inhibit viral replication by interfering with the formation of the E1/E2 complex.

A third object of the invention is the description of compositions consisting of the appropriate E1 and E2 proteins, and suitable assay reagents that facilitate their combination to yield an assay mixture that effects E1/E2 complex formation.

A fourth object of the invention is the description of an assay employing two early phase papillomavirus proteins, 68 kD E1 and 48 kD E2, that form a E1/E2 complex, and an appropriate nucleic acid sequence that binds the E1 or E2 proteins alone or as part of a complex. Since the E1/E2 complex bound to the nucleic acid sequence is involved in the initiation of viral DNA replication, inhibitors of replication can be identified by their capacity to prevent formation of the complex associated with the sequence.

A fifth object of the invention is a description of compositions consisting of the appropriate E1 and E2 proteins and nucleic acid sequences, and suitable assay reagents that facilitate their combination to yield an assay mixture that effects E1/E2 complex formation in the presence of the sequence.

A sixth object of the invention is the description of methods for treating animals suffering from papillomavirus diseases.

These and other objects of the invention will become apparent on a full consideration of the following disclosure.

DETAILED DESCRIPTION OF THE INVENTION

Figure 1:
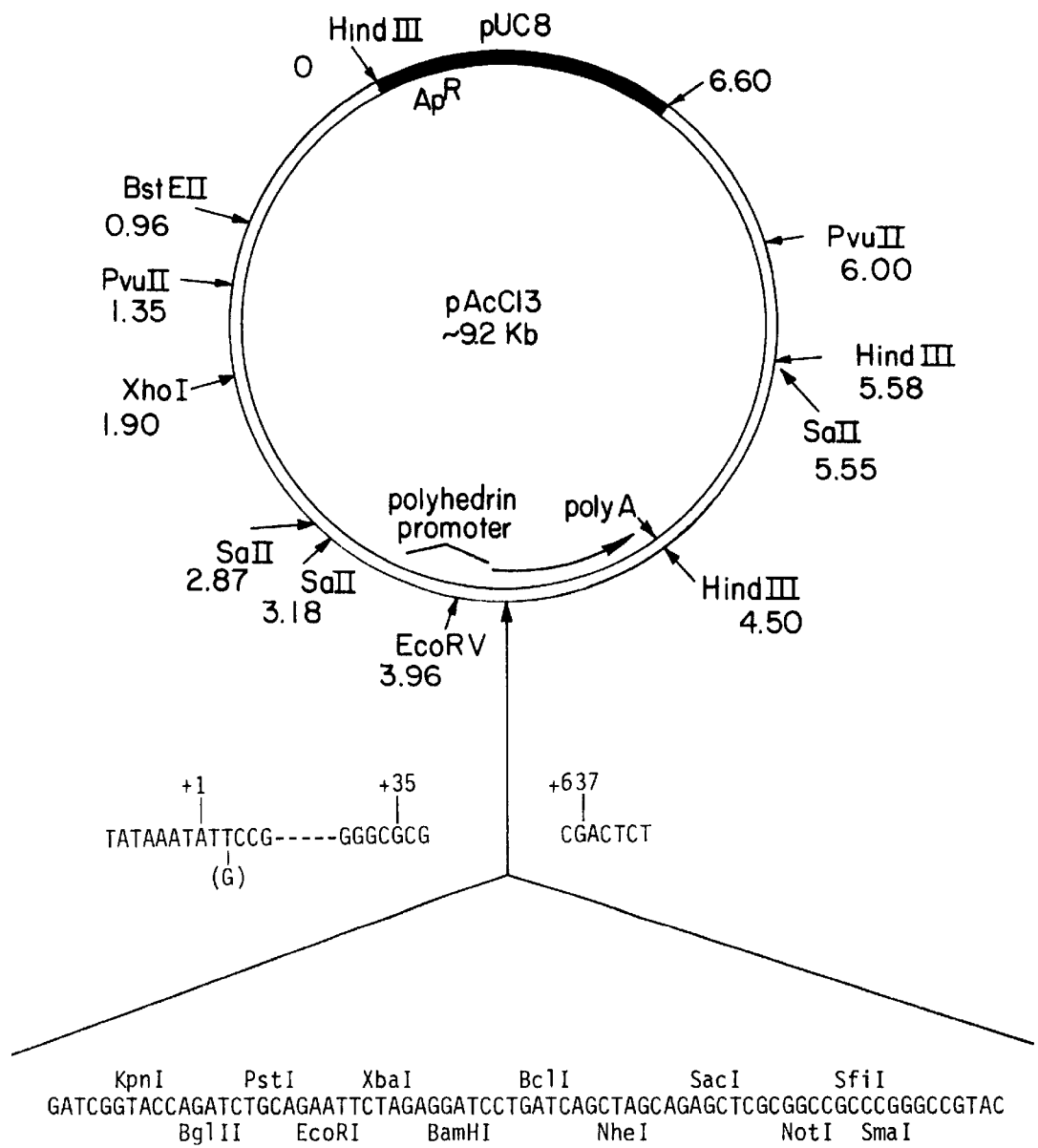
FIG. 1 which includes SEQ ID NOS: 1–4, shows the plasmid pAcC13, a transfer vector that was used to produce recombinant baculovirus encoding the appropriate E1 or E2 proteins.

The invention described herein draws on previously published work and pending patent applications. By way of example, such work consists of scientific papers, patents or pending patent applications. All of these publications and applications, cited previously or below are hereby incorporated by reference.

Definitions

"E1 and E2" refer to those papillomavirus proteins encoded by the E1 and E2 open reading frames that have molecular mass of about 68 kD and 48 kD, respectively, and that form a complex that binds to papillomavirus DNA, and consequently are involved in initiating viral DNA synthesis. Since a key aspect of the invention described herein is the discovery that E1 and E2 form a hithertofor unsuspected complex, it is intended within this definition to encompass similar papillomavirus proteins that may have different molecular mass, but that behave in a functionally related manner. It will further be appreciated that fragments of E1 and E2 are intended to come within the definition.

"Control sequences" refers to DNA sequences necessary for the expression of an operably linked coding sequence in a particular host organism. The control sequences which are suitable for procaryotes, for example, include a promoter, optionally an operator sequence, a ribosome binding site, and possibly, other as yet poorly understood, sequences. Eucaryotic cells are known to utilize promoters, polyadenylation signals, and enhancers.

"Expression system" refers to DNA sequences containing a desired coding sequence and control sequences in operable linkage, so that hosts transformed with these sequences are capable of producing the encoded proteins. In order to effect transformation, the expression system may be included on a vector; however, the relevant DNA may then also be integrated into the host chromosome.

As used herein "cell", "cell line", and "cell culture" are used interchangeably and all such designations include progeny. Thus "transfolrants" or "transformed cells" includes the primary subject cell and cultures derived therefrom without regard for the number of transfers. It is also understood that all progeny may not be precisely identical in DNA content, due to deliberate or inadvertent mutations. Mutant progeny which have the same functionality as screened for in the originally transformed cell, are included. Where indistinct designations are intended, it will be clear from the context.

As used herein, the term "pharmaceutically acceptable" refers to a carrier medium which does not interfere with the effectiveness of the biological activity of the active ingredients and which is not toxic to the hosts to which it is administered. The administration(s) may take place by any suitable technique, including subcutaneous and parenteral administration, preferably parenteral. Examples of parenteral administration include intravenous, intraarterial, intramuscular, and intraperitoneal, with intravenous being preferred.

As used herein, the term "prophylactic or therapeutic" treatment refers to administration to the host of the papillomavirus medicament. If it is administered prior to exposure to the virus, the treatment is prophylactic (i.e., it protects the host against infection), whereas if administered after infection or initiation of the disease, the treatment is therapeutic (i.e., it combats the existing infection or cancer).

As used herein the term "papillomavirus disease" refers to any kind of disease caused by the virus, including cancers and warts.

Production of Papillomavirus E1 and E2 Proteins

The invention described herein shows that the papillomavirus 68 kD E1 replication protein and 48 kD E2 transactivator protein form a E1/E2 complex that binds to the viral origin of replication and thus would effect viral DNA synthesis. Hereinafter, reference to E1 and E2 will be understood to denote these proteins or proteins with similar molecular mass and function. The key functional characteristic being the capacity of the proteins to form a complex that is involved in initiating viral DNA synthesis. Inhibitors of E1/E2 complex formation would inhibit viral replication and are appropriately used as medicaments for the treatment of papillomavirus diseases. Thus, to assay for medicaments by their capacity to inhibit E1/E2 complex formation, appropriate sources of the E1 and E2 proteins are required to carry out the assay. E1 and E2 are preferably produced recombinantly and isolated using various known biochemical purification protocols or modifications thereof.

In general terms, the production of a recombinant E1 or E2 typically involves the following:

First, a DNA is obtained that encodes the proteins and the expression of the proteins is obtainable in an appropriate expression system capable of processing them. This sequence should be in excisable and recoverable form.

The excised or recovered coding sequence is then preferably placed in operable linkage with suitable control sequences in a replicable expression vector. The vector is used to transform a suitable host and the transformed host cultured under favorable conditions to effect the production of the recombinant protein.

Each of the foregoing steps can be done in a variety of ways. The constructions for expression vectors operable in a variety of hosts are made using appropriate replicons and control sequences, as set forth below. Suitable restriction sites can, if not normally available, be added to the ends of the coding sequence so as to provide an excisable gene to insert into these vectors.

The control sequences, expression vectors, and transformation methods are dependent on the type of host cell used to express the gene. Generally, procaryotic, yeast, insert, or mammalian cells are presently useful as host. Although procaryotic hosts are in general the most efficient and convenient for the production of recombinant proteins, eucaryotic cells, and, in particular, mammalian cells or insect cells are preferred for their processing capacity.

Procaryotes most frequently are represented by various strains of *E. coli*. However, other microbial strains may also be used, such as bacilli, for example, *Bacillus subtilis*, various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar et al., 1977, *Gene* 2:95. pBR322 contains genes for ampicillin and tetracycline resistance, and thus provides additional markers which can be either retained or destroyed in constructing the desired vector. Commonly used procaryotic control sequences, which are defined herein to include promoters for transcription initiation, optionally with an operator, along with ribosome binding site sequences, include such commonly used promoters as the beta-lactamase (penicillinase) and lactose (lac) promoter systems (Chang et al., 1977, *Nature* 198:1056), the tryptophan (trp) promoter system (Goeddel et al., 1980, *Nucleic Acids Res.* 8:4057) and the lambda derived $P_L$ promoter (Shimatake et al., 1981, *Nature* 292:128), and N-gene ribosome binding site, which has been made useful as a portable control cassette, U.S. Pat. No. 4,711,845, issued Dec. 8, 1987 and incorporated herein by reference in its entirety, which comprises a first DNA sequence that is the $P_L$ promoter operably linked to a second DNA sequence corresponding to the $N_{RBS}$ upstream of a third DNA sequence having at least one restriction site that permits cleavage within 6 bp 3' of the $N_{RBS}$ sequence. U.S. Pat. No. 4,666,848, issued May 19, 1987 and incorporated herein by reference in its entirety discloses additional vectors with enhanced expression capabilities. Also useful is the phosphatase A (phoA) system described by Chang et al., in European Patent Publication No. 196,864, published Oct. 8, 1986, incorporated herein by reference. However, any available promoter system compatible with procaryotes can be used.

The E1 and E2 nucleic acid sequences may be cloned into a vector by using primers to amplify the sequence which contains restriction sites on their non-complementary ends according to the general methods as disclosed in U.S. Pat. Nos. 4,683,195 issued Jul. 28, 1987, 4,683,202 issued Jul. 28, 1987 and 4,800,159 issued Jan. 24, 1989 the latter of which is incorporated herein by reference in its entirety. A modification of this procedure involving the use of the heat stable *Thermus aquaticus* (Taq) DNA polymerase has been described and characterized in European Patent Publication No. 258,017, published Mar. 2, 1988 incorporated herein by reference in its entirety. Also useful is the Thermal Cycler instrument (Perkin-ElmerCetus) which has been described in European Patent Publication No. 236,069, published Sep. 9, 1987 also incorporated herein by reference in its entirety.

Generally, the nucleic acid sequence to be cloned is treated with one oligonucleotide primer for each strand and an extension product of each primer is synthesized which is complementary to each nucleic acid strand. An alternative to the use of plasmid DNAs encoding the E1 and E2 proteins as template for PCR is the use of RNA from any cell producing these proteins as template for PCR as described in U.S. Pat. No. 4,800,159. If RNA is the available starting material, the extension product synthesized from one primer when separated from its complement can serve as template for synthesized of the extension product of the other primer. As previously mentioned, each primer contains a restriction site on its 5' end which is the same as or different from the restriction site on the other primer. After sufficient amplification has occurred the amplification products are treated with the appropriate restriction enzyme(s) to obtain cleaved products in a restriction digest. The desired fragment to be cloned is then isolated and ligated into the appropriate cloning vector.

For portions of vectors derived from cDNA or genomic DNA which require sequence modifications, site-specific primer directed mutagenesis is used. This technique is now standard in the art, and is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Construction of suitable vectors containing the desired E1 and E2 coding sequence employs standard ligation and restriction techniques which are well understood in the art. Isolated vectors, DNA sequences, or synthesized oligonucleotides are cleaved, tailored, and relegated in the form desired.

Site specific DNA cleavage is performed by treating with suitable restriction enzyme(s) under conditions which are generally understood in the art, and the particulars of which are specified by the manufacturer of these commercially available restriction enzymes. See, e.g., New England Biolabs, Product Catalog. In general, about 1 μg of plasmid or DNA sequence is cleaved by one unit of enzyme in about 20 μl of buffer solution. In the examples herein, typically, an excess of restriction enzyme is used to insure complete digestion of the DNA substrate. Incubation times of about 1–2 hours at about 37° C. are workable, although variations can be tolerated. After each incubation, protein is removed by extraction with phenol/chloroform, and may be followed by ether extraction, and the nucleic acid recovered form aqueous fractions by precipitation with ethanol followed by chromatography using a Sephadex G-50 spin column. If desired, size separation of the cleaved fragments may be performed by polyacrylamide gel or agarose gel electrophoresis using standard techniques. A general description of size separations is found in *Methods in Enzymology,* 1980, 65:499–560.

Restriction cleaved fragments may be blunt ended by treating with the large fragment of *E. coli* DNA polymerase I, that is, the Klenow fragment, in the presence of the four deoxynucleotide triphosphates (dNTPs) using incubation times of about 15–25 minutes at 20 to 25° C. in 50 mM Tris pH 7.6, 50 mM NaCl, 6 mM $MgCl_2$, 6 mM DTT and 10 mM dNTPs. After treatment with Klenow, the mixture is extracted with phenol/chloroform and ethanol precipitated. Treatment under appropriate conditions with S1 nuclease results in hydrolysis of single-stranded portions.

Ligations are performed in 15–30 μl volumes under the following standard conditions and temperatures: 20 mM Tris-Cl pH 7.5, 10 mM $MgCl_2$, 10 mM DTT, 33 μg/ml BSA, 10 mM-50 mM NaCl, and 1 mM ATP, 0.3–0.6 (Weiss) units T4 DNA ligase at 14° C. for "sticky end" ligation, or for "blunt end" ligations 1 mM ATP was used, and 0.3–0.6 (Weiss) units T4 ligase. Intermolecular "sticky end" ligations are usually performed at 33–100 μg/ml total DNA concentration. In blunt end ligations, the total DNA concentration of the ends is about 1 μM.

In vector construction employing "vector fragments," the vector fragment is commonly treated with bacterial alkaline phosphatase (BAP) in order to remove the 5' phosphate and prevent religation of the vector. BAP digestions are conducted at pH 8 in approximately 150 mM Tris, in the presence of $Na^+$ and $Mg^{+2}$ using about 1 unit of BAP per μg of vector at 60° C. for about 1 hour. Nucleic acid fragments are recovered by extracting the preparation with phenol/chloroform, followed by ethanol precipitation. Alternatively, religation can be prevented in vectors which have been double digested by additional restriction enzyme digestion of the unwanted fragments.

In the constructions set forth below, correct ligations are confirmed by first transforming the appropriate *E. coli* strain with the ligation mixture. Successful transformants are selected by resistance to ampicillin, tetracycline or other antibiotics, or using other markers depending on the mode of plasmid construction, as is understood in the art. Miniprep DNA can be prepared from the transformants by the method of D. Ish-Howowicz et al., 1981, *Nucleic Acids Res.* 9:2989 and analyzed by restriction and/or sequenced by the dideoxy method of F. Sanger et al., 1977 *PNAS (USA),* 74:5463 as further described by Messing et al., 1981 *Nucleic Acids Res.,* 9:309, or by the method of Maxam et al., 1980 *Methods in Enzymology,* 65:499.

Host strains used in cloning in M13 consists of *E. coli* strains susceptible to phage infection, such as *E. coli* K12 strain DG98 are employed. The DG98 strain has been deposited with ATCC Jul. 13, 1984 and has accession number 1965.

Depending on the host cell used, transformation is done using standard techniques appropriate to such cells. The calcium treatment employing chloride, as described by S. N. Cohen, 1972 *PNAS (USA)* 69:21 10, or the $RbCl_2$ method described in Maniatis et al., 1982, *Molecular Cloning: A Laboratory Manual* Cold Spring Harbor Press, p. 254 was used for procaryotes.

As mentioned above, numerous recombinant systems are available for the cloning and expression of E1 and E2. However, the preferred system is baculovirus. Thus to exemplify the invention, E1 and E2 were produced using bovine papillomavirus constructs expressed in baculovirus. The baculovirus transfer vectors employed herein, for example pAcC13, are derived from transfer vectors which have been described by G. E. Smith et al., 1983, above. These vectors were originally constructed by cloning the AcNPV EcoRI-1 fragment containing the polyhedrin gene into the EcoRI site of *E. coli* plasmid pUC8 as described by Vieira et al., 1982, *Gene* 19:259–268. A family of plasmids having single BamHI cloning sites at various locations in the polyhedrin gene were created as described by Smith et al., 1983, above. The most used of these, pAc373, has a unique BamHI site 50 base pairs downstream from the polyhedrin cap site, that is to say, 8 base pairs before the polyhedrin ATG translation initiation codon (Luckow and Summers 1988, in *Biotechnology,* 6:47).

The baculovirus vector pAcC13 was constructed from another transfer vector, pAcC12, which in turn was constructed from preexisting vectors, particularly pAc311 and pAc373, as described by Luckow and Summers in *Biotechnology,* 6:47 (1988); U.S. Pat. No. 4,745,051; and EPA 127,839. Additional details are presented by Summers and Smith in "A Manual of Methods for Baculovirus Vectors and Insect Cell Culture Procedures", Texas Agricultural Experiment Station Bulletin No. 1555, May, 1987. All of these references are hereby incorporated in their entirety.

Briefly, pAcC12 was constructed as described below, and as described in U.S. patent application, Ser. No. 07/230,761, filed Aug. 10, 1988, entitled Gap Gene Sequences and Diagnostic Uses Thereof. The transfer vector pAc311 was site-directed mutagenized using M13 mutagenesis techniques to convert the polyhedrin gene initiation codon, ATG, to ATT. The resulting vector was designated pVL941, and is described in detail by Luckow and Summers in *Virology,* titled "High Level of Expression of Non-Fused Foreign Genes with Autographa Californica Nuclear Polyhedrosis Virus Expression Vectors". A polylinker was inserted into pVL941 at a unique BamHI site 30 base pairs downstream of the ATT sequence. pVL941 was digested with BamHI, and the polylinker, consisting of two complementary self-annealed oligomers, EK129 and EK130, having the sequences shown below, ligated to produce the vectors pAcC8 and pAcC9 that carry the polylinker in different orientations. The polylinker has a restriction site for EcoRI, as well as for other restriction enzymes.

EK129:

5'GATCCACCATGGAGCTCGAGATCTA-GAATTCTGCAGCCCGGGTACCGATC3' SEQ ID NO: 5. EK130:

5'GATCGGTACCCGGGCTGCAGAATTCTA-GATCTCGAGCTCCATGGTGGATC3' SEQ ID NO: 6.

Because pAcC8 and pAcC9 have two EcoRI restriction sites, one in the polylinker and the other in the plasmid DNA, it was desirable to remove the plasmid EcoRI site. This was achieved using the transfer vector pAc373. pAc373 is similar to pAc311 except that the nucleotide sequences spanning the polyhedrin start codon differ. Thus, the EcoRI site was removed from pAc373 by digesting the vector to completion with EcoRI, and the ends made blunt using the Klenow fragment under the appropriate reaction conditions. Following ligation and transformation into *E. coli* DH 5, colonies were identified that lacked the EcoRI site by restriction analysis of miniprep DNA.

pAc373 lacking the EcoRI site was further modified by incorporating the polylinker consisting of the oligomers, EK129 and EK130, shown above, by digesting the vector with BamHI, followed by ligating the oligomers. The resulting vectors, pAcC6 and pAcC7, contain the polylinker in different orientations.

The final construct, pAcC12, was generated from pAcC7 and pAcC9 as shown in U.S. patent application, Ser. No. 07/230,761. These vectors contain the polylinker in the same orientation. Both vectors were digested with BstEII and EcoRI and the resulting fragments electrophoretically purified. The BstEII/EcoRI fragment of pAcC7 containing the pUC 8 sequences, and partial polylinker sequences was ligated to the large BstEII/EcoRI fragment of pAcC9. This latter fragment contains the ATT sequence and the remaining polylinker sequences.

Finally, pAcC13 was derived from pAcC12 as described by Munemitesu, S. et al., 1990, *Mol. Cell. Bio.*, 10:5977–5982, or Quilliam, L. et al., 1990, *Mol. Cell. Biol.*, 10:2901–2908. FIG. 1 shows a map of the plasmid. Briefly, pAcC13 was derived from pAcC12 by replacing the KpnI fragment between 4 and 4.5 map units with a synthetic oligonucleotide containing the following polylinker:

0.1%. Sodium azide may also be included in the solution at a concentration of 0.02%. The blots are washed, and subjected to autoradiography using X-ray film.

Baculovirus expressing E2 was prepared similarly. The details of the E2 expression vector constructs and the purification of the E2 protein by specific oligonucleotide affinity chromatograph are described by Knight and Botchan, 1991, *PNAS (USA)*.

To produce recombinant E1, Sf9 cells were infected with 5–10 PFU of recombinant virus per cell. Methods for infecting and growing Sf9 cells are well known in the art, and detailed procedures can be found in M. Summers and G. Smith. in "A Manual of Methods for Baculovirus Vectors and Insect Cell Culture Procedures", Texas Agricultural Experiment Station, Bulletin No. 1555 (May, 1987) or in EPO 127,839 to G. E. Smith and M. D. Summers. Preferred media and culturing conditions can be found in co-pending, commonly owned U.S. patent application, Ser. Nos. 77,181, entitled "Airlift Insect Cell Culture, filed Jul. 24, 1987; 77,303, entitled "Serum Free Media for the Growth of Insect Cells and Expression of Products Thereby", and 77,189, entitled "Lipid Microemulsions for Culture Media". These publications and patent applications are hereby incorporated by reference.

Sf9 cells were infected at $1–15\times10^6$ cells per ml and were harvested at 48 hours post infection. Infected cell pellets were frozen in liquid nitrogen and stored at $-70°$ C. Cells were lysed by thawing and immediately suspended in 5 pellet volumes of hypo buffer (10 mM Hepes pH 7.4 5 mM KCl, 1 mM $MgCl_2$, 1 mM DTT, 10 mg/ml Leupeptin, 1 mM 5'GTACCAGATCTGCAGAATTCTAGAGGATCCTGATCAGCTAGCAGA
GCTCGCGGCCGCCCGGGCCGTAC-3' SEQ ID NO: 7.

As a source of bovine papillomavirus E1 ORF, plasmid pMTE1DM was used to produce the transfer vector pAcE1. This construct was derived from plasmid pMTE1, which is described in detail by Shaw Sun et al., 1990, *J. of Virology*, 64:509. pMTE1DM is essentially identical to pMTE1 with the exception that pMTE1DM has a G to A substitution at nucleotide 1236. This substitution prevents production of the spliced M protein. Thus, the 68 kD E1 protein produced by pMTE1DM maintains bovine papillomavirus DNA as an extrachromosomal element. Next, the transfer vector pAcE1 was produced by removing the E1 encoding XbaI fragment from pMTE1DM and inserting the fragment into the XbaI site of the transfer vector pAcC13. Note that the E1 encoding XbaI fragment from pMTE1DM is downstream of the baculovirus polyhedrin promoter.

To generate recombinant virus, 2 μg of transfer vector was co-transfected with 1 μg of wild type DNA into Sf9 cells as described by Summers and Smith in "A Manual of Methods for Baculovirus Vectors and Insect Cell Culture Procedures", Texas A & M Press: 1986. Recombinant virus (occlusion-negative) was isolated from the transfection supernatant by plaque purification as described by Smith et al., 1983, *Mol. Cell. Biol.*, 3:2156–2165. Protein production was monitored by Western analysis. The preferred electrophoresis procedure is Western blot gel analysis as described by Bumette, 1981, *Anal. Bio. Chem.*, 112:195. The Western blots are blocked, washed, and probed preferably in 10 mM sodium phosphate buffer containing 150 mM sodium chloride (pH 7.4), with 0.1% bovine serum albumin (w/v), and 0.1% ovalbumin (w/v). In addition, a detergent is preferably employed such as Tween 20 at a concentration of about PMSF). A nuclear fraction was prepared with 18 strokes of a dounce homogenizer (B-pestle), and the mixture was then clarified by centrifugation at 5,000×g for 10 minutes (HB4 rotor). The pellet was washed twice with Nucleic Wash buffer (20 mM Tris-HCL PH 8.0, 1 MM DTT, 1 mM EDTA, 1 mM PMSF, 10 μg/ml Leupeptin, 10% Sucrose), and suspended in 5 pellet volumes of Hypo buffer. NaCl was slowly added to a final concentration of 0.3M and the mixture was slowly agitated at 4° C. for 30 minutes. Following centrifugation at 10,000 rpm for 10 minutes, in a HB4 rotor, the supernatant was applied to a DEAE Sepharose fast flow column (Pharmacia) equilibrated in buffer A (20 mM Tris-HCl pH 8.0, 1 mM EDTA, 5% glycerol, 0.05% Triton X-100) containing 0.3M NaCl (A/300). The column was rinsed with 3 volumes of A/300 and this was fraction along with the DEAE flow-through fraction were adjusted to 0.2M NaCl with buffer A. The individual fractions were then sequentially applied to a Phosphocellulose P-11 matrix (Whatmann) equilibrated in A/200. The column was washed with A/200 and eluted stepwise with buffer A containing 0.4M followed by 1M NaCl. These individual fractions were then dialysed against A/200 (approximately 4 changes of 500 ml for 25 minutes each) and adjusted to 0.2M NaCl with buffer A if necessary. Each pool was individually applied to a Mono Q 5/5 column (Pharmacia) equilibrated in 25 mM Tris pH 8.0, 200 mM NaCl, 1 mM EDTA, 5% glycerol, 0.1% Triton X-100. The column was rinsed with this buffer. This was followed by a step elution with 1M NaCl in the same buffer. Fractions containing E1 were identified by Western blotting, pooled, and the indicated amounts used to illustrate the invention.

Isolation of Papillomavirus DNA and Binding of E1, E2, or E1/E2 Complexes Thereto To demonstrate the binding of E1, E2, or a complex consisting of E1 and E2 to papillomavirus DNA, DNA is preferably used that has sequence homology to the origin of papillomavirus DNA replication that binds E2. Also, it is noteworthy that the papillomavirus genome contains multiple E2 binding sites which may be employed. Indeed, the bovine papillomavirus genome contains about 17 E2 binding sites. Thus, the ability of purified E1, E2, or a mixture of these proteins to bind to papillomavirus origin DNA was studied using labelled DNA fragments as described below.

The plasmid, pUC237 contains papillomavirus origin sequences on the XbaI-SmaI fragment (n.t. #6132–945) of BPV-1 cloned into pUC18 Yang and Botchan, 1990, *J. Virology*, 64:5903–5911. To prepare origin DNA to demonstrate E1 binding in the presence of E2, the plasmid was digested with HindIII, ClaI, and EcoRI, treated with calf intestinal alkaline phosphatase and subsequently kinased with $\gamma$-$^{32}$P ATP. The labelled DNA was extracted with phenol, chloroform, and precipitated with ethanol. 4 µl of partially purified E1 was incubated with 25 ng of labelled pUC237 in the presence or absence of various amounts of purified E2 in a final volume of 50 µl. Binding buffer consisted of 10 mM Hepes pH 7.4, 100 mM KCl, 1 MM MgCl$_2$, 5% glycerol, 1 mM DTT, 20 µg/ml salmon sperm DNA. The final ionic strength of the reaction was kept between 160 mM and 200 mM. Reactions were incubated at 37° C. for 40–50 minutes after which they were turned to room temperature. 1.5 µl anti E1 polyclonal sera was then added and the incubation continued for 20 minutes. 100 µl of a 10% slurry of protein A Sepharose (Pharmacia) equilibrated in 50 mM Hepes pH 7.4, 200 mM NaCl, 5 mM EDTA, 0.05% Triton X-100, 20 µg/ml salmon sperm DNA was added, and the reactions were rocked for 50 minutes at room temperature. The beads were pelleted and washed 3 times with 50 mM Hepes pH 7.4, 200 mM NaCl, 5 mM EDTA, 0.05% Triton X-100. To avoid additional dilution of reactions with anti E2 tissue culture supernatants, the E2 monoclonal B202 was prebound to protein A Sepharose beads (50 µl B202 per 100 µl 10% protein A Sepharose) prior to its addition of the reactions. Alternatively, 10 µg of pure B202 was added, and the immunoprecipitations were performed as described for anti E1. B202 is available from Elliot Androphy at the New England Medical Center, Tufts University School of Medicine Department of Dermatology, 750 Washington Street, Boston, Mass. 02111. The final pellets were resuspended in 1% SDS, 25 mM EDTA and held at 65° C. for 15 minutes. Reactions were then adjusted to 20 mM Tris pH 8.0 and Proteinase K was added to 50 µg/ml. After 60 minutes at 37° C., 5 µg of carrier tRNA was added and the reactions were extracted with phenol, chloroform, and precipitated with ethanol. DNA fragments purified from immune complexes were electrophoresed on 5% native polyacrylamide gels. The gels were dried onto DE-81 paper (Whatman) and exposed to Kodak XAR film.

Figure 2:
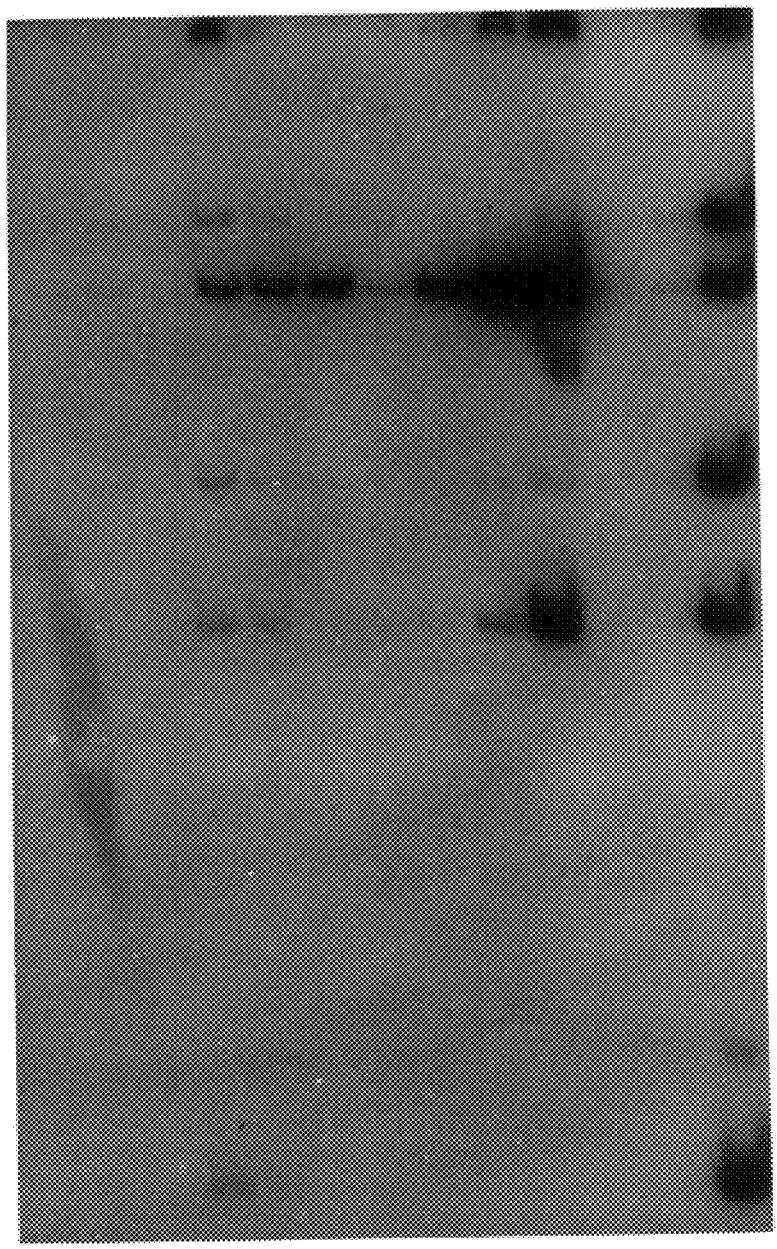
FIG. 2 shows that the 48 kD E2 protein stimulates the specific DNA binding activity of E1. A set amount of E1 and varying amounts of E2 were incubated with a mixture of end labelled DNA fragments. Protein DNA complexes were immunoprecipitated with either anti-E1 or anti-E2, as denoted. Labelled DNA bound in the immune complexes was fractionated on 5% native polyacrylamide gels visualized by autoradiography. The lane marked input contains an aliquot of the starting mixture. The numbers above each lane denotes microliters of either substantially purified E1 or pure E2 (2.5 µg/ml).

FIG. 2 shows that substantially purified E1 exhibits a weak affinity for the 1.4 kD band which contains E2 binding sites 5–13. Further, it is shown in the figure that this weak binding is stimulated by the presence of the 48 kD E2 protein. That is to say, in the presence of a fixed amount of E1, increasing amounts of E2 causes increasing amounts of the DNA fragment to be bound. Control experiments revealed that in the absence of E1 protein, binding of E2 to the DNA fragment is not detected as revealed by immunoprecipitation experiments using anti-E1 antibody, but that it can be visualized if immunoprecipitated with anti-E2 antibody. At higher concentrations of E2, a smaller fragment containing weaker E2 binding sites is also observed with anti-E2 antibody. Thus, it is apparent that the E2 48 kD protein significantly facilitates the association of the E1 protein with DNA.

Figure 3:
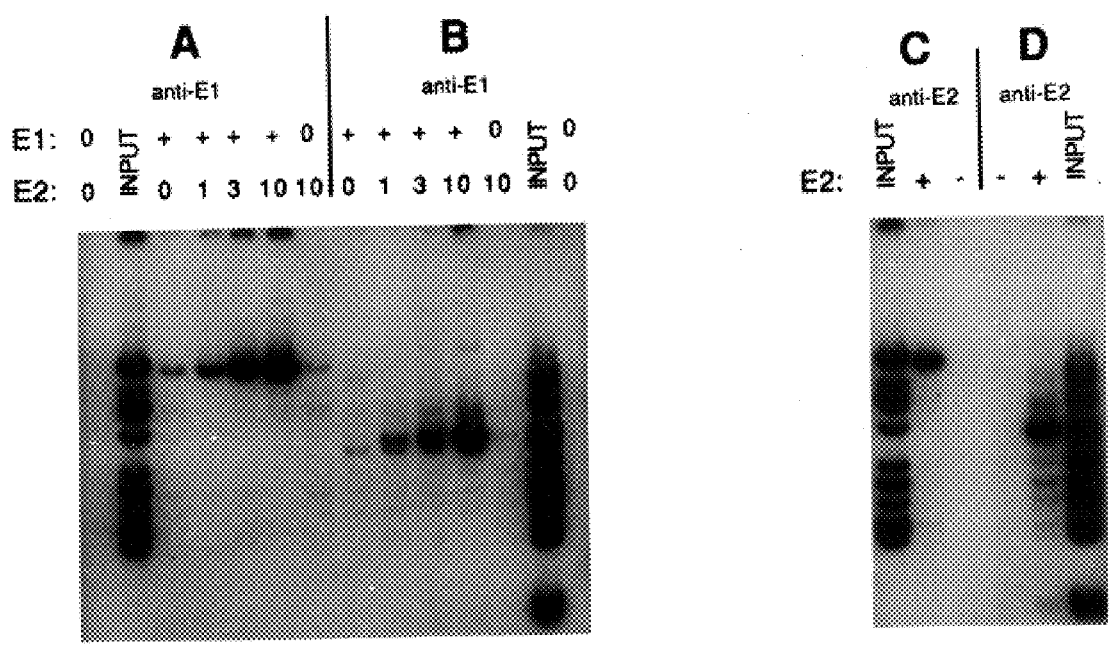
FIGS. 3A–3D show that the E1/E2 complex binds to the BPV-1 origin of replication. A set amount of substantially purified E1 and varying amounts of pure E2 were incubated with different mixtures of labelled DNA. Protein-DNA complexes were immunoprecipitated with anti-E1 or anti-E2. Labelled DNA present in the complexes was fractionated on native polyacrylamide gels and visualized by autoradiography. pUC237 was digested with DdeI and ClaI in panels A and C, or DdeI and TaqI in panels B and D.

The specific DNA fragment bound by the E1/E2 complex in the previous experiment spanned nucleotides 7480–945. To further delineate the cis elements recognized by the E1/E2 complex, binding substrates were prepared and digested with different restriction enzymes. Protein DNA complexes were then immunoprecipitated with either anti-E1 or anti-E2 and processed as described previously. Purified E2 protein (immunoprecipitated with anti-E2 ) bound to a 596 bp fragment in the Dde/Cla mixture and to a 319 bp fragment in the Dde/Taq mixture (3C). This 319 bp fragment spans nucleotides 7477–7796 and contains E2 binding sits 5–10. DNA sequences involved in the control of transcription (Spalholz, B. et al., 1987, *J. Virol*, 61:2128–2137) as well as the origin of replication are present on this fragment (Yang, L. and Botchan, M., 1990, *J. Virol.*, 64:5903–5911). FIG. 3 display the results of binding experiments immunoprecipitated with anti-E1. Partially purified E1 protein displays a weak specific DNA binding activity in the absence of E2. Addition of increasing amounts of purified E2 results in increased binding to either the 596 bp Dde.Cla fragment or the 319 bp Taq fragment. This demonstrates that the E1/E2 complex specifically binds to sequences which contain the E2RE1 transcriptional enhancer element.

E1/E2 Complex Formation.

Having demonstrated that the appropriate early phase proteins can bind to papillomavirus DNA, studies were undertaken to show the existence of the E1/E2 complex. This consisted of infecting Sf9 insect cells with baculoviruses expressing either E1, E2, or both viruses and subsequently analyzing the cells to ascertain if E1/E2 complex formation had occurred. This was accomplished as follows. Sf9 cells were labelled with $^{35}$S methionine and cellular extracts were passed through DEAE Sepharose to remove endogenous nucleic acids. Anti-E1 or anti-E2 antibodies were used to form immunoprecipitates which were analyzed by electrophoresis in combination with autoradiograms.

The immune complexes were subjected to electrophoresis on an SDS polyacrylamide gel and visualized on autoradiograms. Molecular weight markers are shown on the right. The numbers in the track labelled "antisera" refer to either anti E1 (1) or anti E2 (2) antibodies. 3×10$^6$ Sf9 cells were transferred from suspension culture to 6 cm plates. The monolayer was then infected with either the E1, E2, or both recombinant baculoviruses (the multiplicity of infection was approximately 10 for the single infections, and 5 of each virus for the coinfection). At 48 hours post infection, the infected cells were starved for 1 hour in Grace's medium, lacking methionine, containing 10% dialyzed fetal calf serum. Cells were labelled for 5 hours in 0.75 ml of media containing 100 µCi of $^{35}$S translabel (ICN). Extracts were prepared by lysing cells in 0.5 ml of 50 mM Hepes pH 7.6, 300 mM NaCl, 1 mM EDTA, 10% glycerol, 0.5% NP40, 10 µg/ml Leupeptin, 1 mM PMSF. The plates were incubated at 0° C. for minutes after which the contents were scraped into a microfuge tube and spun for 2 minutes. The supernatant was transferred to a vessel containing 0.2 ml settled bed volume of DEAE Sepharose Fast flow (Pharrnacia) equilibrated in lysis buffer. The mixture was rotated at 4° C. for 5 minutes, spun in a microfuge, and the resin was washed with 0.4 ml of lysis buffer. 0.2 ml of the pooled supernatants was diluted with 0.3 ml of 50 mM Hepes pH 7.6, 200 mM NaCl, 1 M EDTA, 10% glycerol. Protein A Sepharose (in lysis buffer containing 100 mM NaCl) prebound with either anti-E1 or anti-E2 antibodies was then added and the reactions were rotated at 4° C. for 1 hour (each reaction received the equivalent of either 6 μl of affinity purified anti-E1 polyclonal antisera or 50 μl of anti E2 B202 tissue culture supernatant). The beads were pelleted in a microfuge and washed 4 times with 50 mM Hepes pH 7.6, 200 mM NaCl, 1 mM EDTA, 10% glycerol, 0.05% NP-40. Pellets were boiled in Laemli buffer and electrophoresed on SDS-polyacrylamide gels. The gels were fixed, dried, and exposed to Kodak XAR film.

Figure 4:
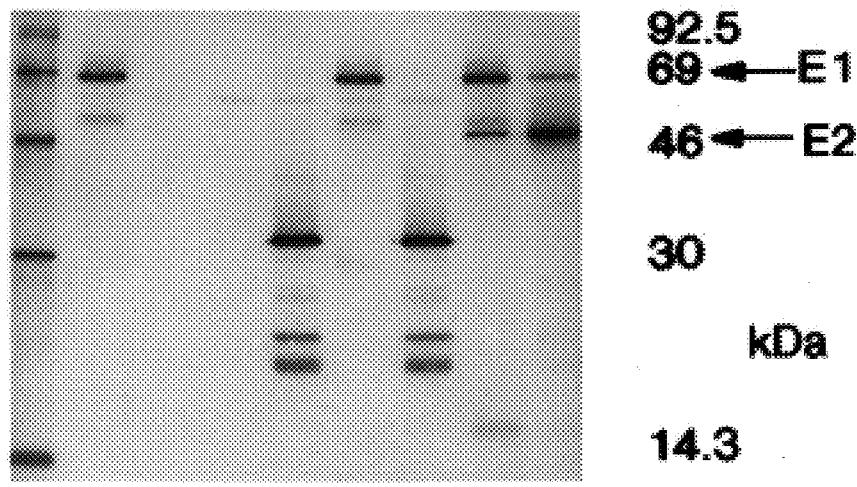
FIG. 4 shows that E2 forms a specific complex with the E1 replication protein.

FIG. 4 shows various immunoprecipitation controls, that is, that anti-E1 precipitates 68 kD E1, while anti-E2 precipitates 48 kD E2. Further, and most importantly, both anti-E1 and anti-E2 immunoprecipitate 68 kD E1 and 48 kD E2 from cells co-infected with both recombinant baculoviruses. Thus, this establishes that E1 and E2 form a physical complex and that such complex forms in the absence of exogenous nucleic acids.

Immunoaffinity Purification of the E1/E2 Complex

Figures 5A, 5B:
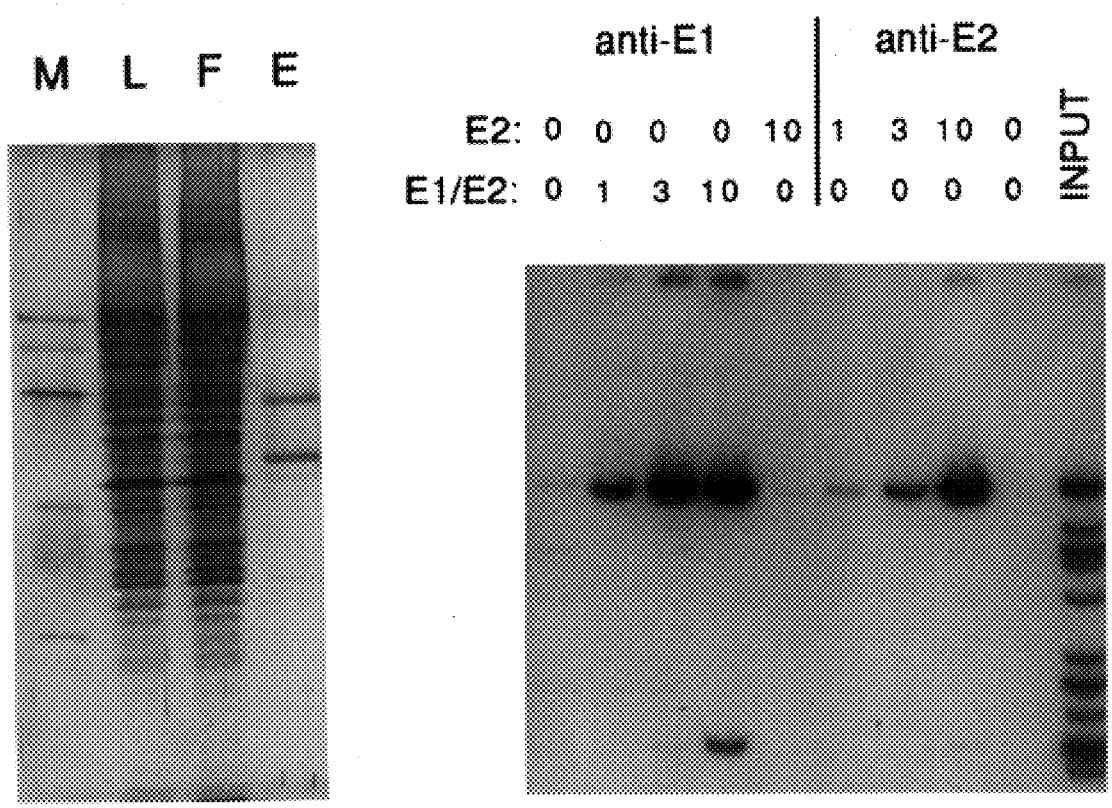
FIG. 5A shows the immunoaffinity purification of the E1/E2 complex.
FIG. 5B shows binding of purified E1/E2 complex to DNA. Purified E1/E2 complex or pure E2 was incubated with an end labelled mixture of DNA fragments (pUC237 digested with DdeI and ClaI). Protein-DNA complexes were immunoprecipitated, processed and visualized as described before.

FIG. 5A shows a SDS polyacrylamide gel of fractions eluted from an immunoaffinity matrix containing immobilized B202 anti E2. L and F refer to the load and flow through respectively, while lane E displays the material eluted from the column. The gel was stained with silver and the MW markers (lane M) are as follows: 200 kD, 116 kD, 97 kD, 68 kD, 45 kD, 30 kD. The 400 mM Phosphocellulose fraction prepared from Sf9 cells coinfected with recombinant E1 and E2 viruses was adjusted to A/200 with buffer A and applied to a column containing immobilized B202. The resin was washed with 10 volumes of A/200, 50 volumes of buffer A+1M LiCl, and reequilibrated with an additional 10 volumes of A/200. Proteins were eluted with 20 mM Triethylamine and fractions were immediately neutralized with ¹⁄₂₀ volume of 1M Hepes pH 7.4. Peak fractions were pooled, snap frozen in a dry ice ethanol bath, and stored at −70° C. The immunoaffinity matrix was constructed by incubating pure B202 antibody with protein A Sepharose in 100 mM Tris pH 8.0 (6 $OD^{280}$ antibody per ml of resin) overnight on a rotator at 4° C. The mixture was washed extensively with 100 mM borate buffer pH 9.0, suspended in 20 mM Dimethylpimelimidate hydrochloride (Pierce), and rotated for 1 hour at room temperature. Unreacted crosslinker was blocked by suspending the beads in 40 mM ethanolamine—HCl pH 8.0 at room temperature. The beads were stored in 100 mM borate buffer pH 8.0 (68, 69).

Isolation of the E1/E2 Complex

To obtain preparative amounts of the E1/E2 complex for biochemical analysis an immunoaffinity purification scheme was developed. Nuclear extracts from insect cell coinfected with both E1 and E2 recombinant baculoviruses were fractionated through DEAE Sepharose and phosphocellulose. Since purified E2 flows through phosphocellulose and a fraction of E1 binds to phosphocellulose, this suggests that E2 is retained on this resin by virtue of its association with E1. The protein fraction eluted from phosphocellulose with 400 mM NaCl was applied to the immunoaffinity matrix containing the E2 monoclonal antibody B202 immobilized on protein A Sepharose. The resin was then washed with 1M LiCl buffer, eluted with high pH, and the fractions were immediately neutralized. FIG. 4A demonstrates that the 68 kD E1 protein and the 48 kD E2 protein were the major protein species eluted from this column, and both were present in stoichiometric amounts by silver staining. Their identity was confirmed by Western analysis (not shown). The stability of the complex to a stringent high salt wash suggests that its formation may be driven by hydrophobic interactions.

The material eluted from this matrix retains its specific DNA binding activity. Increasing amounts of the complex bound increasing amounts of the 596 bp Dde/Cla fragment when immunoprecipitated with anti-E1 (FIG. 5B). At higher protein concentrations, a 140 bp fragment containing the weaker E2 binding sites is also bound.

Identification of Papillomavirus Medicaments

Papillomavirus medicaments can be identified by their ability to prevent E1/E2 complex formation, the disruption of the complex when formed, or binding of E1 or E2 alone or as a complex to papillomavirus DNA. Thus, those assays presented above that reveal E1/E2 complex formation, or binding of E1 or E2 alone or as a complex to papillomavirus DNA may be employed to identify such medicaments by incorporating them in the assay mixture and monitoring their effect on the selected event.

Exemplary medicaments would be peptides that inhibit the binding of E1 to E2. Preferably, such peptides would be derived from the amino terminal end of E2, and more preferably from the first 162 amino acids. Examples of peptides in this region include the following:

$NH_2$-ELSKTEFGDEPWSL-COOH SEQ ID NO: 8.
$NH_2$-DTSWDRYMSEPKR-COOH SEQ ID NO: 9.
$NH_2$-FKKGARVVEVEFDGNASNTNWYTV-COOH SEQ ID NO: 10.

To be effective against papillomavirus diseases, for example skin diseases, one or more of the peptides, alone or in combination, can be formulated in a suitable cream that would be applied to the diseased area. The dose and administration regime will be a function of whether the peptides are being administered therapeutically or prophylactically, and the patient's medical history. Typically, the amount of peptide administered per dose will be in the range of about 0.1 to 25 mg/kg of body weight, with the preferred dose being about 0.1 to 10 mg/kg of patient body weight.

For parenteral administration, the peptides will be formulated in an injectable form combined with a pharmaceutically acceptable parenteral vehicle. Such vehicles are well known in the art and examples include water, saline, Ringer's solution, dextrose solution, and solutions consisting of small amounts of the human serum albumin. The preparation of such solutions is within the skill of the art. Typically, the peptides will be formulated in such vehicles at a concentration of about 2–8.0 mg/ml to about 100 mg/ml.

In addition to those assays described above that utilize immunoprecipitation to identify medicaments that inhibit papillomavirus replication, it will be appreciated by those skilled in the art that other assay formats can also be employed. For example a preferred assay is an ELISA assay as described by Smeenk, R. J. T., et al., 1987, *Arthritis Rheum*, 30:607. For a description of additional ELISA assay methods see Langone, J. and Van Vinakis, H., 1983, *Methods of Enzymology*, 92, Part E.

An example of using an ELISA assay would consist of binding the desired early phase protein, for example E1, either directly or indirectly, to a solid support. E1 can be bound to the support via antibody. Next, under the appropriate reaction conditions of pH, salt, etc., E2 can be added in the presence or absence of a compound being tested for papillomavirus medicament properties. Those compounds that have such properties will inhibit or reduce E1/E2 complex formation compared to the controls. The extent of complex formation can be preferably monitored using a labelled molecule that binds to E2. This would most preferably be a labelled antibody specific for E2.

The antibodies employed in the present invention can be immobilized on any appropriate solid test support by any appropriate technique. The solid test support can be any suitable insoluble carrier material for the binding of antibodies in immunoassays. Many such materials are known in the art, including, but not limited to, nitrocellulose sheets or filters; agarose, resin, plastic (e.g. PVC or polystyrene) latex, or metal beads; plastic vessels; and the like. Many methods of immobilizing antibodies are also known in the art. See, e.g., Silman et al., 1966, Ann. Rev. Biochem., 35: 873; Melrose, 1971, Rev. Pure & App. Chem., 21: 83; Cuatrecaas et al., 1971, Meth. Enzym., 22. Such methods include covalent coupling, direct adsorption, physical entrapment, and attachment to a protein-coated surface. In the latter method, the surface is first coated with a water-insoluble protein such as zein, collagen, fibrinogen, keratin, glutelin, etc. The antibody is attached by simply contacting the protein-coated surface with an aqueous solution of the antibody and allowing it to dry.

Any combination of support and binding technique which leaves the antibody immunoreactive, yet sufficiently immobilizes the antibody so that it can be retained with any bound antigen during a washing, can be employed in the present invention. A preferred solid test support is a plastic bead.

As discussed above, the assay of the present invention employs a labelled second antibody. In the example discussed above this antibody binds to E2, but the assay could be run by affixing E2 to a solid support, and using a labelled antibody that binds to E1. In any event, the label can be any type that allows for the detection of the antibody when bound to a support. Generally, the label directly or indirectly results in a signal which is measurable and related to the amount of label present in the sample. For example, directly measurable labels can include radio-labels (e.g. 125I, 35S, 14C, etc.). A preferred directly measurable label is an enzyme, conjugated to the antibody, which produces a color reaction in the presence of the appropriate substrate. (e.g. horseradish peroxidase/o-phenylenediamine). An example of an indirectly measurable label is antibody that has been biotinylated. The presence of this label is measured by contacting it with a solution containing a labeled avidin complex, whereby the avidin becomes bound. to the biotinylated antibody. The label associated with the avidin is then measured. A preferred example of an indirect label is the avidin/biotin system employing an enzyme conjugated to avidin, the enzyme producing a color reaction as described above.

Whatever label is selected, it results in a signal which can be measured and is related to the amount of label in a sample. Common signals are radiation levels (when radioisotopes are used), optical density (e.g. when enzyme color reactions are used) and fluorescence (when fluorescent compounds are used). It is preferred to employ a nonradioactive signal, such as optical density (or color intensity) produced by an enzyme reaction. Numerous enzyme/substrated combinations are known in the immunoassay art which can produce a suitable signal. See, e.g., U.S. Pat. Nos. 4,323,647 and 4,190,496, the disclosures of which are incorporated herein.

In the ELISA assays described above, anti-E1 and anti-E2 antibody can be polyclonal or monoclonal. The procedures for generating polyclonal antibody are particularly well known in the art, while monoclonal antibody can be produced by several methods. See for example, the procedure of Kohler and Milstein described in Nature, 256:495 (1975), or modified procedures such as those shown by Fendly, et al, 1987, Hybridoma, 6:359; Buck, et al., 1988, In Vitro, 18:377. In vitro techniques are generally described by Luben, R. and Mohler, M., 1980, Molecular Immunology, 17:635, Reading, C. Methods in Enzymology, 121 (Part One):18, or Voss, B., 1986, Methods in Enzymology, 121:27.

Briefly, a suitable procedure would consist of immunizing mice with 1 mg/ml of E1 or E2. The immunization is carried out in complete Freund's adjuvant. Two additional immunizations, or boosts, are performed at monthly intervals without adjuvant, and one month after the last boost the mice are given an I.V. boost of 10 $\mu$g of either E1 or E2. Three days after the I.V. boost, mice are sacrificed, their spleens removed, and the spleenocytes isolated and fused to an immortalized drug selectable myeloma partner cell line. Numerous such myeloma lines are known in the art, most of which are incapable of growth in HAT supplemented cell culture media. A typical myeloma cell line is SP-2/0Ag 14. Thus, the hybridomas are formed by combining splenocytes and myeloma cells in a 5:1 ratio, which generally consists of $2\times10^6$ myeloma cells to $1\times10^7$ splenocytes. The cell mixture is pelleted, media removed and fusion affected by the addition of 1.0 ml of 40% (v/v) solution of polyethylene glycol 1500 by dropwise addition over 60 seconds at room temperature, followed by a 60 second incubation at 37° C. To the cell suspension with gentle agitation is added 9 ml of Dulbecco's Modified Eagles medium over 5 minutes. Cell clumps in the mixture are gently resuspended, the cells washed to remove any residual PEG and plated in microliter plates at about $2\times10^5$ cells/well in DMEM supplemented with 20% fetal calf serum. After 24 hours, the cells are fed a 2x solution of hypoxanthine and azaserine selection medium. Media from wells that exhibit positive cell growth can be assayed for anti-E1 or anti-E2 using assays known in the art, which can detect soluble, or nonsoluble antigens, and are shown by Langone, J. and Van Vinakis, H., Methods of Enzymology, 92, Part E (1983).

Regardless of whether the antibody is polyclonal or monoclonal it is desirable to purify the antibody by standard techniques as is known in the art, or described by Springer, 1980, Monoclonal Antibodies:194, (Eds. Kennett, T. McKearn and K. Bechtol, Plenum Press, New York. Generally this consists of at least one ammonium sulfate precipitation of the antibody using a 50% ammonium sulfate solution. Antibody affinity columns may also be used.

Although any similar or equivalent methods and materials may be employed in the practice or testing of the present invention, the preferred methods and materials are now described.

Having described what the applicants believe their invention to be, the following examples are presented to illustrate the invention, and are not to be construed as limiting the scope of the invention. For example, variation in the source, type, or method of producing antibodies; different labels and/or signals; test supports of different materials and configurations; different immobilization methods may be employed without departing from the scope of the present invention.

Deposition of Cultures

The biological materials used in the above examples illustrate the present invention and are deposited in the American Type Culture Collection (ATCC), 12301

Parklawn Drive, Rockville, Md., USA, under the terms of the Budapest Treaty. The deposit dates and the accession numbers are given below:

| Virus | Deposit Date | Accession No. |
|---|---|---|
| E1 Baculovirus | October 16, 1991 | VR2341 |
| E2 Baculovirus | October 16, 1991 | VR2342 |

This deposit was made under the Budapest Treaty and will be maintained and made accessible according to the provisions thereof.

Availability of the deposited cell lines are not to be construed as a license to practice the invention in contravention of the rights granted under the authority of any government in accordance with its patent laws.

The present invention has been described with reference to specific embodiments. However, this application is intended to cover those changes and substitutions which may be made by those skilled in the art without departing from the spirit and the scope of the appended claims.

We claim:

1. A method of identifying medicaments for treating papillomavirus diseases, comprising the steps of:
   a) mixing E1 and E2 in solution to form a complex of E1 and E2;
   b) measuring E1 and E2 complex formation; and
   c) repeating steps (a) and (b) in the presence of said medicaments.

2. A method of identifying medicaments for treating papillomavirus diseases, comprising the steps of:
   a) mixing E1 and E2 with papillomavirus DNA under conditions that cause said E1 and E2 to form a complex of E1 and E2 bound to said DNA;
   b) measuring complex formation of E1 and E2 bound to said DNA; and
   c) repeating steps (a) and (b) in the presence of said medicaments.

3. A method of identifying medicaments for treating papillomavirus diseases, comprising the steps of:
   a) mixing E1 with papillomavirus DNA under conditions that cause said E1 to bind to said DNA;
   b) measuring E1 binding to said DNA; and
   c) repeating steps (a) and (b) in the presence of said medicaments.

* * * * *

```
SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
         (A) LENGTH: 13 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:1:

TATAAATATT CCG                                                          13

(2) INFORMATION FOR SEQ ID NO:2:

(i) SEQUENCE CHARACTERISTICS:
         (A) LENGTH: 7 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:2:

GGGCGCG                                                                  7

(2) INFORMATION FOR SEQ ID NO:3:

(i) SEQUENCE CHARACTERISTICS:
         (A) LENGTH: 7 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:3:

CGACTCT                                                                  7

(2) INFORMATION FOR SEQ ID NO:4:

(i) SEQUENCE CHARACTERISTICS:
         (A) LENGTH: 73 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:4:
```

```
GATCGGTACC AGATCTGCAG AATTCTAGAG GATCCTGATC AGCTAGCAGA GCTCGCGGCC          60

GCCCGGGCCG TAC                                                            73

(2) INFORMATION FOR SEQ ID NO:5:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GATCCACCAT GGAGCTCGAG ATCTAGAATT CTGCAGCCCG GGTACCGATC                    50

(2) INFORMATION FOR SEQ ID NO:6:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GATCGGTACC CGGGCTGCAG AATTCTAGAT CTCGAGCTCC ATGGTGGATC                    50

(2) INFORMATION FOR SEQ ID NO:7:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GTACCAGATC TGCAGAATTC TAGAGGATCC TGATCAGCTA GCAGAGCTCG CGGCCGCCCG          60

GGCCGTAC                                                                  68

(2) INFORMATION FOR SEQ ID NO:8:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Glu Leu Ser Lys Thr Glu Phe Gly Asp Glu Pro Trp Ser Leu
  1               5                  10

(2) INFORMATION FOR SEQ ID NO:9:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:
```

```
Asp Thr Ser Trp Asp Arg Tyr Met Ser Glu Pro Lys Arg
1               5                   10

(2) INFORMATION FOR SEQ ID NO:10:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Phe Lys Lys Gly Ala Arg Val Val Glu Val Glu Phe Asp Gly Asn Ala
1               5                   10                  15

Ser Asn Thr Asn Trp Tyr Thr Val
                20
```